United States Patent [19]
Bokoch

[11] Patent Number: 5,244,916
[45] Date of Patent: Sep. 14, 1993

[54] INHIBITION OF RESPIRATORY BURST USING POSTTRANSLATIONAL MODIFICATION INHIBITORS

[75] Inventor: Gary M. Bokoch, Encinitas, Calif.

[73] Assignee: The Scripps Research Institute, La Jolla, Calif.

[21] Appl. No.: 829,766

[22] Filed: Jan. 31, 1992

[51] Int. Cl.$^5$ .................. A61K 31/015; A61K 31/19; A61K 31/35

[52] U.S. Cl. .................................. 514/460; 514/557; 514/763

[58] Field of Search ...................... 514/460, 557, 763

[56] References Cited

PUBLICATIONS

Curnutte, et al., *J. Biol. Chem.* 262: 6450-2 (1987).
Curnutte, et al., *J. Biol. Chem.* 262: 5563-5569 (1987).
Clark, *J. Infect. Dis.* 161: 1140-7 (1990).
Buss, et al., *Mol. Cell. Biol.* 11: 1523-1530 (1991).
Bokoch, et al., *J. Cell. Biol.* 106: 1927-1936 (1988).
Quinn, et al., *Nature* 342: 198-200 (1989).
Bokoch, et al., *Science* 254: 1794-6 (1991).
Gibbs, *Cell* 65: 1-4 (1991).
Knaus, et al., *Science* 254: 1512-1515 (1991).
Maltese, et al., *J. Biol. Chem.* 265: 2148-2155 (1990).
Maltese, *FASEB* 4: 3319-3328 (1990).
Hancock, et al., *EMBO J.* 10: 641 646 (1991).
Hancock, et al., *Cell* 57: 1167-1177 (1989).
Casey, et al., *PNAS USA* 86: 8323-8327 (1989).
Schafer, et al., *Science* 245: 379-384 (1989).
Jackson, et al., *PNAS USA* 87: 3042-3046 (1990).
Endo, et al., *FEBS* 72: 323-326 (1976).
Alberts, et al., *PNAS USA* 77: 3957-3961 (1985).
Elson, et al., *Carcinogenesis* 9: 331-2 (1988).
Crowell, et al., *J. Biol. Chem.* 266: 17679-17686 (1991).

*Primary Examiner*—Leonard Schenkman
*Attorney, Agent, or Firm*—Douglas A. Bingham; Thomas Fitting; April C. Logan

[57] ABSTRACT

The present invention relates to the use of posttranslational modification inhibitors, such as isoprenylation inhibitors, to inhibit activation of phagocyte NADPH oxidase and respiratory burst. Therapeutic compositions containing various inhibitors, and methods of using same, are also disclosed.

14 Claims, 2 Drawing Sheets

1    2    3    4    5

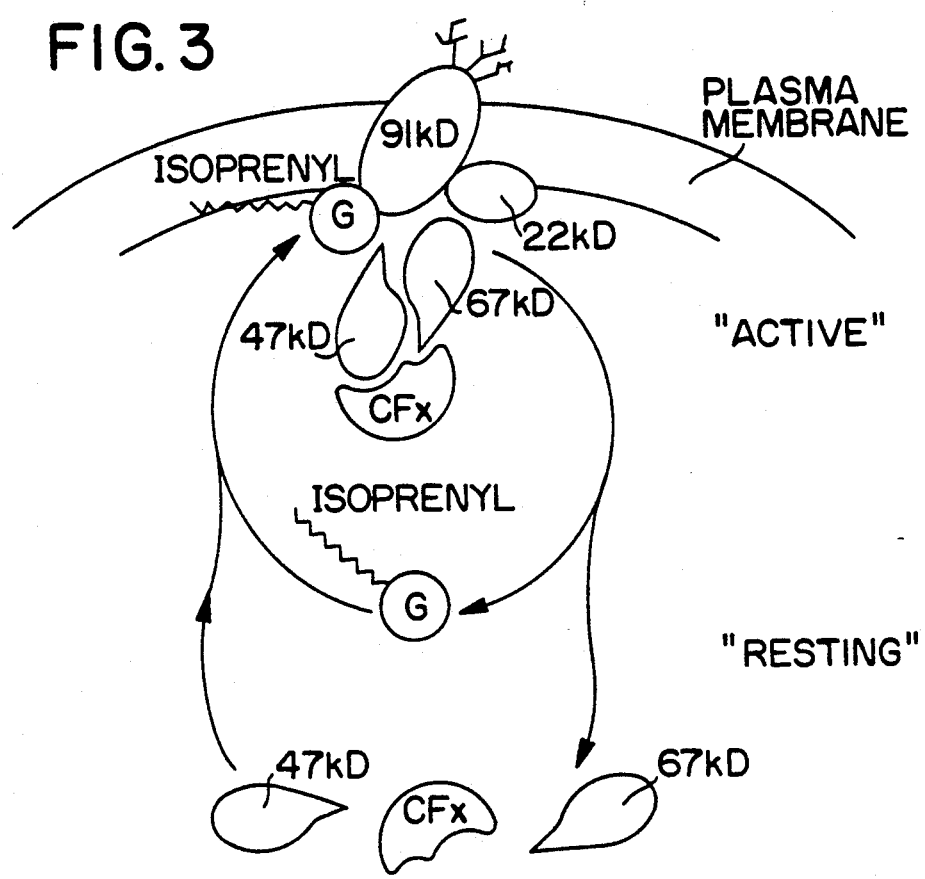

INHIBITION OF RESPIRATORY BURST USING POSTTRANSLATIONAL MODIFICATION INHIBITORS

GOVERNMENT INTEREST

"This invention was made with the support of the United States Government, and the United States Government has certain rights in the invention pursuant to National Institutes of Health Contract GM 39434."

TECHNICAL FIELD

This invention relates to the use of posttranslational modification inhibitors, such as isoprenylation inhibitors, to inhibit activation of phagocyte NADPH oxidase and respiratory burst.

BACKGROUND OF THE INVENTION

Neutrophils serve as the body's primary cellular defense against bacterial infection. One of the mechanisms by which neutrophils destroy invading microorganisms is through the generation of various toxic oxygen metabolites via the so-called "respiratory burst" (Babior, *NEJM* 298: 659–668 (1978)). "Respiratory burst" is the name given the phenomenon that occurs when neutrophils undergo a large burst in respiration in which oxygen is converted to superoxide anion ($O_2^-$), the initial product of the respiratory burst. Superoxide anion is generated by an NADPH oxidase found in neutrophils and other phagocytes (Babior, supra (1978; Clark, *J. Infect. Dis.* 161 : 1140-7 (1990)). This "enzyme" is actually a miniature electron transport chain consisting of multiple plasma membrane- and cytosollocalized protein components. The oxidase is apparently dormant in resting neutrophils, but acquires catalytic activity when the cells are stimulated. (See Curnutte, et al., *J. Biol. Chem.* 262: 6450-2 (1987).) This dramatic increase in oxidative metabolism triggered by phagocytosis or exposure to certain inflammatory mediators is also characteristic of mononuclear phagocytes and eosinophils, but it is best understood in neutrophils. (See Clark, *J. Infect. Dis.* 161: 1140-7 (1990).)

The importance of the NADPH oxidase for the neutrophil's antibacterial capacity is evidenced by patients with the inherited disorder chronic granulomatous disease. The neutrophils of patients with this disorder are unable to generate superoxide anion and are subject to persistent, severe bacterial infections, which often result in life-threatening episodes or even death (Clark, supra (1990); Curnutte, in *Phagocytic Defects II: Abnormalities of the Respiratory Burst*, Hematology/Oncology Clinics of North America, 241-252 (1988)). It has been shown that several forms of this disease result from genetic defects in one of the various protein components of the NADPH oxidase system (Curnutte, suora (1988)).

The mechanism by which the NADPH oxidase is activated by inflammatory stimuli is not well understood but appears to involve the assembly of the various components of the NADPH oxidase at the plasma membrane level to form an "active" complex (Clark, suora (1990)). The processes involved in the translocation of cytosolic oxidase components to the membrane also remain to be defined. There is evidence that a GTP-binding protein is involved in regulating the activation process (Quilliam and Bokoch, in *Cellular and Molecular Mechanisms of Inflammation*, Vol. 2 (1991); Cochrane and Gimbrone, eds., Academic Press, San Diego, CA). Indeed, a GTP-binding protein known as Rap1A (see Quilliam, et al., *Mol. Cell. Biol.* 10: 2901-8 (1990)) has been shown to bind to the cytochrome b component of the NADPH oxidase (Quinn, et al., *Nature* 342: 198-200 (1989); Bokoch, et al., *Science* 254: 1794-6 (1991)). Rac2 has now been identified as a stimulatory regulator of the oxidase in human neutrophils (See Knaus, et al., *Science* 254: 1512-1515 (1991).

The low molecular weight GTP-binding proteins (LMWG) represent a rapidly growing superfamily of GTPases that regulate a wide variety of cellular processes (Hall, Science 249: 635–40 (1990)). These proteins consist of a GTP-binding monomer with a molecular weight of 19,000–28,000 and have properties that distinguish them from the various receptor-coupled G protein $\alpha$ subunits, including their lack of associated $\beta$/gamma subunits. Although the LMWG can vary greatly in their overall amino acid sequences, they exhibit a number of features that are common to each. These include (1) common structural motifs; (2) regulation by extrinsic factors that modulate whether the protein is in a GTP- or GDP-state; and (3) posttranslational processing by isoprenylation, proteolytic truncation, and carboxymethylation. The latter is directed by a CAAX consensus motif found at the carboxyl terminus of all known isoprenylated proteins, where C is a cysteine residue, A is any aliphatic amino acid, and X is variable (Maltese, *FASEB* 4: 3319-3328 (1990)). proteins that affect the guanine-nucleotide binding and hydrolysis activity of various LMWG have also been identified, including guanosine triphosphate activating proteins (GAPs), proteins that stimulate guanine nucleotide exchange, and proteins that inhibit guanosine diphosphate (GDP) dissociation. (See Bokoch, et al., *Science* 254: 1794–6 (1991) and references cited therein.)

Posttranslational processing involves an initial isoprenylation at the cysteine residue via a thioether bond between the protein and a C15 (farnesyl) or C20 (geranylgeranyl) isoprenyl moiety. This is followed by proteolytic truncation of the protein, removing the three amino acids distal to the isoprenylated cysteine. The newly-exposed COOH-terminal cysteine is then carboxymethylated. For the Ras proteins, each of these processing steps has been shown to be an important determinant of Ras binding to the plasma membrane (Hancock, et al., *EMBO J.* 10: 641-646 (1991]; Hancock, et al., *Cell* 57: 1167-1177 (1989)) and isoprenylation is critical for proper expression of the transforming activity of oncogenic Ras (Casey, et al., *PNAS USA* 86: 8323-8327 (1989); Schafer, et al., Science 245: 379-384 (1989); Jackson, et al., *PNAS USA* 87: 3042-3046 (1990)).

Various studies have identified a multiplicity of cellular proteins that appear to be covalently modified by isoprenyl groups (Maltese, supra (1990); Glomset, et al., *Trends Biochem. Sci.* 15: 139-142 (1990)). The electrophoretic patterns of these proteins is remarkably similar from one cell to another, and the proteins generally fall into two size classes. A group of 44-69 kD isoprenylated proteins are largely localized to the nucleus and the associated nuclear matrix. Within this group are the nuclear lamins (Maltese, supra (1990); Schafer, *supra* (1989); Wolda, et al., *J. Biol. Chem.* 263: 5977-6000 (1988)). A second class of 20-24 kD isoprenylated proteins are more widely distributed within the cell and appear to represent the LMWG (Maltese, et al., *J. Biol. Chem.* 265: 2148-2155 (1990)). A common feature of all known isoprenylated proteins is the presence of a CAAX motif at the carboxyl terminus. This sequence appears to represent a signal for protein isoprenylation and is present in most of the LMWG that have been identified (Maltese, FASEB 4: 3319–3328 (1990); Glomset, et al., *Trends Biochem. Sci.* 15: 139–142 (1990)).

The importance of $O_2$—in bacterial killing is evidenced by the chronic infections and even death observed in patients with severe neutropenia, chronic granulomatous disease, and other disorders of neutrophil function. However, the inappropriate or excessive formation of $O_2$—and its byproducts can both initiate and exacerbate inflammation. Inflammatory diseases and/or secondary inflammation resulting from a primary disorder are serious health problems. Therefore, the development of means to intervene in these processes in a specific manner is of great therapeutic interest. In addition, identification of key proteins involved in NADPH oxidase activation in phagocytic cells and the development of means to inhibit or otherwise regulate these proteins is of equal significance.

BRIEF SUMMARY OF THE INVENTION

Pharmacologic agents able to block protein isoprenylation have been identified. These inhibitors, which include compactin and lovastatin, among others, are capable of inhibiting the enzyme 3-hydroxy-3-methylglutaryl-coenzyme A (HMG-CoA) reductase. (See, e.g., Maltese, *supra* (1990); Endo, et al., *FEBS* 72: 323–326 (1976); Alberts, et al., *PNAS USA* 77: 3957–3961 (1985).) This enzyme synthesizes mevalonic acid, an immediate precursor of the isoprenoids. In the studies described herein, the effect of inhibitors of protein isoprenylation on the ability of DMSO-differentiated HL-60 cells to undergo a respiratory burst in response to receptor and nonreceptor stimuli was examined.

Enzyme as used herein refers to a protein or polypeptide capable of accelerating or producing by catalytic action some change in a substrate for which it is often specific. The term may also be used herein to indicate an electron transport chain consisting of multiple plasma membrane- and cytosol-localized protein components. The term inhibitor is used herein to refer to a composition that associates with an oxidase, reductase, or other enzyme in such a manner as to inhibit the normal function of the enzyme. Such inhibition can be effected by a variety of ways, including binding of the inhibitor to a site on the enzyme such that the substrate binding site is blocked through steric hinderance; binding of the inhibitor composition to the active site of the enzyme and thus preventing access of substrate to the active site, thus preventing its activity; binding of the inhibitor to the enzyme in such a manner that changes the secondary or tertiary structure of the enzyme and therefore inhibits its activity (allosteric effects); and other ways.

Compactin, as well as lovastatin, caused an inhibition of NADPH oxidase activation at micromolar concentrations that could be attributed to the ability of this compound to inhibit the pathway leading to protein isoprenylation. Using these drugs, it was possible to localize the lovastatin- and compactin-sensitive component to the cytosolic fraction of differentiated HL-60 cells. Preliminary experiments now indicate that the inhibitory effects of these drugs may be specifically reversed by reconstitution of the system with purified Rac2, demonstrating that this is likely to be the compactin- or lovastatin-sensitive target (data not shown).

Therefore, the present invention contemplates agents capable of preventing or inhibiting posttranslational modification of proteins or polypeptides involved in regulation of the NADPH oxidase system, particularly posttranslational modification of GTP-binding proteins. Posttranslational modification includes, without limitation, isoprenylation, phosphorylation, proteolytic truncation, carboxymethylation, and palmitylation, for example.

Polypeptide and peptide are terms used interchangeably herein to designate a linear series of no more than about 50 amino acid residues connected one to the other by peptide bonds between the alpha-amino and carboxy groups of adjacent residues. Protein is a term used herein to designate a linear series of greater than 50 amino acid residues connected one to the other as in a polypeptide.

The present invention also contemplates agents capable of inhibiting the activation of NADPH oxidase in phagocytic cells, as well as methods of using those agents. In another aspect, the invention discloses uses for agents capable of inhibiting the isoprenylation of GTP-binding proteins, particularly low molecular weight GTP-binding proteins (LMWG). In addition, new uses for various compounds, including compactin and lovastatin, are contemplated, born out of the discovery that administration of these compounds inhibits isoprenylation of GTP-binding proteins.

The present invention thus contemplates a method of inhibiting respiratory burst in patients in need of such treatment, comprising administering an effective amount of a posttranslational modification inhibitor, such as an isoprenylation-inhibiting composition, to the patient The composition may comprise lovastatin, compactin, fluoromevalonate, and other compounds, drugs or prodrugs which specifically block isoprenylation, carboxymethylation, and other posttranslational modifications, and which will not modify the synthesis of cholesterol. In addition, the composition may comprise terpenes, and more preferably monoterpenes, such as limonene, perillic acid, dihydroperillic acid, and other terpene metabolites compositions according to the present invention may further comprise a pharmaceutically acceptable carrier or excipient.

In one embodiment, the invention contemplates that the composition comprises lovastatin, and further, that the amount of lovastatin administered is in the range of 0 mg to about 200 mg per day. In a preferred embodiment, the amount of lovastatin administered is in the dosage range of about 20 mg to about 80 mg per day. In yet another preferred embodiment, the amount of lovastatin administered is in the dosage range of about 10 mg to about 40 mg per day. In another variation, the composition comprises compactin, which is preferably administered in the dosage range of 0 mg to about 200 mg per day. More preferably, the amount of compactin is in the range of about 20 mg to about 80 mg per day. In yet another preferred embodiment, the amount of compactin administered is in the dosage range of about 10 mg to about 40 mg per day.

Another aspect of the invention contemplates the administration of terpene compositions, preferably monoterpenes, such as limonene and its derivatives, including perillic acid and dihydroperillic acid. In one variation, the administered composition is limonene, preferably d-limonene, which is administered in an amount sufficient to raise the limonene concentration in the blood of the patient to at least 0.05 mM. More preferably, limonene is administered in an amount sufficient to raise the limonene concentration in the blood of the patient to at least 0.1 mM, and more preferably, to at least 1.0 mM. In yet another variation, the amount of limonene administered is an amount sufficient to raise the limonene concentration in the blood of said patient to at least 5 mM. It is further preferred that the limonene concentration in the blood of the patient does not exceed 50 mM. These same dosage ranges preferably apply to other terpenes, including terpene derivatives and metabolites, such as perillic acid and dihydroperillic acid. (See, e.g., Crowell, et al., *J. Biol. Chem.* 266: 17679–17686 (1991), and references cited therein ) Concentrations of limonene and its metabolites appropriate for inhibition of protein isoprenylation may also be similar to those used for chemotherapeutic applications, e.g., serum levels approaching about 0.1 mM. (See, e.g., Elson, et al., *Carcinogenesis* 9: 331-2 (1988), or Crowell, et al., *supra* (1991).)

The invention also contemplates that the disclosed compositions may be administered via various means, with the preferred means of administration being oral administration. In another aspect, the invention contemplates that the disclosed compositions target a GTP-binding protein.

BRIEF DESCRIPTION OF THE DRAWINGS

FIG. 3 illustrates a hypothetical model depicting the potential cycling of an isoprenylated LMWG (G) between a cytosolic form in the "resting" oxidase and a membrane-associated form in the "active" oxidase. 91 kD and 22 kD represent the subunits of the oxidase-associated cytochrome b; 47 kD and 67 kD represent other known and as yet unidentified (CFx) cytosolic NADPH oxidase components.

DETAILED DESCRIPTION OF THE INVENTION

Figure 1:
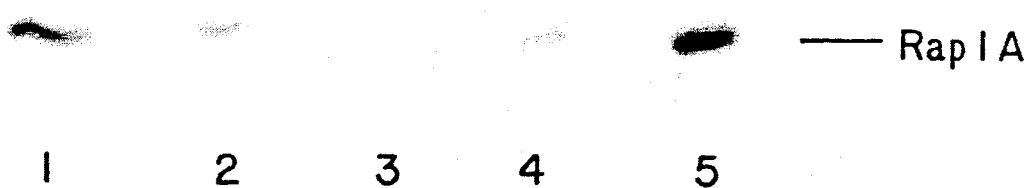
FIG. 1 illustrates the results of a Western blot analysis of Rap1 in HL-60 subcellular fractions. The fractions illustrated include untreated HL-60 membrane (lane 1); 10 μM compactin-treated HL-60 membrane (lane 2); untreated HL-60 cytosol (lane 3); 10 μM compactin-treated HL-60 cytosol (lane 4); and about 300ng Rap1A standard (lane 5).

It is now possible to inhibit the activation of phagocyte NADPH oxidase and respiratory burst via use of inhibitors of posttranslational modification, such as isoprenylation inhibitors, as it has now been found that isoprenylation regulates GTP-binding proteins and regulates respiratory burst. Inhibitors of the present invention include, without limitation, isoprenylation inhibitors such as compactin, lovastatin, and limonene.

Moreover, our related finding that the inhibition due to blockade of protein isoprenylation can be reconstituted with the GTP-binding protein, Rac2, further supports the hypothesis that key regulatory molecules can provide specific targets for agents capable of inhibiting their posttranslational modification, which includes isoprenylation, proteolytic truncation, carboxymethylation, and palmitylation or phosphorylation. (See Knaus, et al., supra (1991).)

As used herein, "respiratory burst" is meant to refer to the phenomenon that occurs when neutrophils undergo a large burst in respiration in which oxygen is converted to superoxide anion ($O_2-$), the initial product of the respiratory burst The term also includes related phenomena such as the production of other toxic oxygen and oxygen-containing derivatives and related inflammatory reaction sequelae Individuals or patients in need of treatment for respiratory burst and its related complications, including inflammation, include individuals who have been exposed to an infection or inflammation-provoking agents or stimuli, such as bacterial or viral pathogens, or other invasive agents which tend to stimulate phagocytic cells. Agents provoking respiratory burst and related phenomena, which indicate a need for the within-described treatment, need not be exogenous agents or stimuli, but may include endogenous agents or stimuli as well. For example, autoimmune conditions in which neutrophils or other phagocytes are activated -- which often results in an inflammatory condition -- may indicate that treatment with posttranslational modification inhibitors is warranted.

As used herein, "posttranslational modification inhibitor" means a compound or composition capable of inhibiting, preventing, or otherwise interfering with the posttranslational modification of a polypeptide or protein. Examples of such inhibitors include compounds or compositions that inhibit isoprenylation, proteolytic truncation, carboxymethylation, palmitylation, and phosphorylation, for example. "Isoprenylation inhibitor" means a compound or composition capable of inhibiting, preventing, or otherwise interfering with the posttranslational isoprenylation of a polypeptide or protein. In various embodiments, "isoprenylation inhibitor" refers particularly to those molecules capable of interfering with or inhibiting the posttranslational isoprenylation of proteins involved in the mevalonic acid metabolism pathway, particularly GTP-binding proteins, and more particularly, LMWG proteins. "Isoprenylation inhibitor" especially refers to those molecules able to inhibit the isoprenylation of LMWG involved in the activation or regulation of NADPH oxidase. Examples of such inhibitors include, without limitation, compactin, lovastatin, monoterpenes, limonene, perillic acid, dihydroperillic acid, and like compounds and compositions containing same.

The terms "composition" or "physiologically administrable composition" as used herein refer to solutions, suspensions and mixtures that are capable of being readily provided into the body of a mammal by parenteral, oral or rectal administration and includes injectable solutions, emulsions and the like.

Compactin and lovastatin are known to block isoprenoid synthesis by inhibiting the enzyme HMG-CoA reductase and should thus be capable of preventing the covalent modification of the LMWG (Maltese, et al., *J. Biol. Chem.* 265: 2148–2155 (1990)). The NADPH oxidase of phagocytes is now believed to be regulated by an apparent LMWG characterized as Rac2 and/or Rac1 (Knaus, et al., supra (1991)). These drugs were tested as a pharmacologic means to intervene in NADPH oxidase activation, based on the hypothesis that if this GTP-binding protein was of the Ras-related or low molecular weight superfamily, then it would likely be posttranslationally isoprenylated.

Thus, the present invention contemplates new uses for compactin, lovastatin, and similar drugs and prodrugs, born out of the discovery that administration of these compounds inhibits the generation of $O_2-$. In addition, the use of other compositions to inhibit respiratory burst and excessive $O_2-$generation is contemplated Methods and compositions useful in inhibiting the activation of NADPH oxidase via inhibiting isoprenylation of Ras-like GTP-binding proteins are also contemplated.

Methods for determining appropriate dosages of the various compositions disclosed herein are well known in the art. For example, there are indirect and direct means which may be used to determine effective dosages. In addition, as therapeutic dosages of lovastatin are known, and as related compositions such as compactin are nearly identical, structurally, with lovastatin, therapeutic dosages for such compositions may reasonably be based thereon. (See, e.g., *Physician's Desk Reference* 43: 1362-5 (1989); The Merck Index 10: 883 (1983).)

Direct and indirect assays for determining the effectiveness, as well as determining the presence of therapeutic levels, of the various compositions disclosed herein include the following examples. Therapeutic levels of isoprenylation inhibitors such as compactin, lovastatin and related compositions, which also have hypocholesterolemic effects, may be determined using known assays for serum cholesterol levels. Other means of determining that therapeutic levels have been achieved in individuals being administered isoprenylationinhibiting compositions include nitro-blue tetrazoline reduction assays and assays for the reduction of cytochrome c, both of which reflect activity of the NADPH oxidase. Volker, et al., in *J. Biol. Chem.* 266: 21515-21522 (1991), and Crowell, et al., J. Biol. Chem. 266: 17679-17686 (1991), describe assays that may be useful in measure the function of enzymes or the level of protein isoprenylation. In addition, a detailed assay measuring the ability of a composition to block protein isoprenylation, and its preferred dosage, is described in Buss, et al., *Mol. Cell. Biol.* 11; 1523-1530 (1991).

The preparation of therapeutic compositions containing isoprenylation inhibitors such as compactin or lovastatin as active ingredients is well understood in the art. While such compositions may be prepared as injectables, either as liquid solutions or suspensions, or in solid form suitable for solution in, or suspension in, liquid prior to injection, oral compositions are generally preferred. The preparation can also be emulsified. Compositions according to the present invention may also be effectively administered topically and/or locally, whereby they may have greater access to the sites of inflammation, i.e., in the lung or in skin lesions. Therefore, compositions contemplated by the present invention may be in the form of creams, ointments, aerosols, or other forms appropriate for presentation of the active ingredient via topical means or inhalataion. The compactin (or other appropriate inhibitor according to the present invention) is often mixed with inorganic and/or organic excipients which are pharmaceutically acceptable and compatible with the active ingredient. Suitable excipients are, for example, water, saline, dextrose, glycerol or the like and combinations hereof. In addition, if desired, the composition can contain minor amounts of pharmaceutically acceptable auxiliary substances such as wetting or emulsifying agents, pH buffering agents which enhance the effectiveness of the active ingredient.

As used herein, the phrase "pharmaceutically acceptable" refers to molecular entities and compositions that do not produce an allergic or similar untoward reaction, such as gastric upset, dizziness and the like, when administered to a human. The terms pharmaceutically acceptable, physiologically tolerable and their grammatical variations, as they refer to compositions, carriers, diluents and reagents, are used interchangeably and represent that the materials are capable of administration to or upon a mammal without the production of untoward physiological effects such as nausea, dizziness, gastric upset and the like.

The compositions are administered in a manner compatible with the dosage formulation, and in a therapeutically effective amount. The quantity to be administered depends on the subject to be treated, and capacity of the subject to utilize the active ingredient. Precise amounts of active ingredient required to be administered depend on the judgment of the practitioner and are peculiar to each individual. However, suitable dosage ranges are of the order of one to several milligrams of active ingredient per individual per day and depend on the route of administration. Suitable regimens for initial administration and booster shots are also variable, but are typified by an initial administration followed by repeated doses at one or more hour intervals, by a subsequent injection or other administration. Alternatively, continuous intravenous infusion sufficient to maintain therapeutically effective concentrations in the blood is contemplated.

The inhibitor (e.g., compactin, lovastatin, or limonene) is conventionally administered subcutaneously, as by injection of a unit dose, for example. The term "unit dose" as used herein refers to physically discrete units suitable as unitary dosages for humans, each unit containing a predetermined quantity of inhibitor calculated to produce the desired therapeutic effect in association with the required excipient.

The inhibitor is administered in a manner compatible with the dosage formulation, and in a therapeutically effective amount Contemplated methods of administration include injection, infusion, implant and the like. The quantity to be administered depends on the subject's ability to use the inhibitor, and the decrease in the blood concentration of activated NADPH oxidase or $O_2-$desired. Precise amounts of inhibitor required to be administered depend on the judgment of the practitioner and are peculiar to each individual. However, suitable compactin dosage ranges are of the order of 0.1 mg to 200mg per day, preferably 1 mg to 120 mg per day, and even more preferably, 20mg to 80mg per day. Administration of the composition is preferably via oral means, albeit other means of administration may be utilized, such as intravascular and intramuscular. Administered dosages will thus vary depending upon the route of administration. Since oral administration is preferred, the effective doses achieved via this mode of administration should be used as a guideline for the practitioner.

Suitable lovastatin dosage ranges are of the order of 0.1 mg to 200 mg per day, preferably 1 mg to 120 mg per day, and even more preferably, 20 mg to 80 mg per day. Suitable dosage ranges for limonene and its metabolites, including perillic acid and dihydroperillic acid, are of the order of an amount sufficient to raise the limonene concentration in the blood of the patient to at least 0.05 mM. Preferably, the amount of limonene administered is an amount sufficient to raise the limonene concentration in the blood of the patient to at least 0.1 mM It is also preferred that the dosage of limonene or its metabolites not produce a blood concentration in excess of 5 mM.

The present invention further contemplates pharmaceutical compositions, preferably sterile and preferably containing a pharmaceutically acceptable carrier or excipient, that can be administered orally to a human subject. Preferred compositions contain isoprenylation inhibiting compounds such as lovastatin, compactin, limonene, or limonene derivatives admixed in a pharmaceutically acceptable excipient wherein the inhibitory compound is the only biologically active ingredient.

It has now been observed that compactin (and lovastatin) markedly inhibited the ability of HL-60 cells to generate $O_2$—in response to both receptor stimuli and downstream activators of the respiratory burst oxidase. The inhibitory effects of compactin occurred at concentrations between 0.4 and 10 $\mu$M. These concentrations are somewhat lower than those that have been previously reported to inhibit the overall isoprenylation of cellular proteins (Maltese, FASEB 4: 3319-3328 (1990); Hancock, et al., Cell 57: 1167-1177 (1989); Casey, et al., supra (1989); Schafer, et al., supra (1989); Jackson, et al., suora (1990)). This may reflect the relative sensitivity of the compactin-sensitive factor in HL-60 cells to the lack of isoprenoid substrate (Repko, et al., J. Biol. Chem. 264: 9945-9952 (1988)). Several pieces of data indicate that the effect of compactin on the oxidase was of a specific nature. At the concentrations of drug used in the within-described studies, HL-60 cell viability was not affected; neither was the ability of these cells to differentiate normally upon exposure to DMSO, as evidenced by analysis of two independent markers of HL-60 differentiation, the N-formyl peptide receptor (Niedel, et al., PNAS USA 77: 1000-10004 (1980)) and the CD14 antigen (Jayaram and Hogg, in Leukocyte Typing IV, Knapp, et al., eds., Oxford Univ. Press, Oxford, U.K., pp. 796-7 (1989)). The effect of compactin is unlikely to be due to inhibition of cholesterol, ubiquinone, or dolichol synthesis, pathways that are also blocked by inhibitors of HMG-CoA reductase. It is known that neutrophils/HL-60 cells do not rely upon endogenous synthesis but largely obtain their cholesterol from exogenous sources. Indeed, since the cells are cultured in 10% fetal calf serum, they are always supplemented with cholesterol and probably dolichol as well. When the compactin-treated HL-60 cells were supplied with additional cholesterol, ubiquinone, or dolichol, the block in NADPH oxidase activity was apparently not overcome. In contrast, cellular responsiveness was totally restored by supplying exogenous mevalonic acid to the cells, indicating that the synthesis of isoprenoids was likely to be the limiting factor that prevented oxidase activation.

A number of components of the neutrophil NADPH oxidase system have been cloned, including p47, p67, and cytochrome b>>s (Volpp, et al., PNAS USA 86: 7195-9 (1989); Leto, et al., Science 248: 727-30 (1990); Royer-Pokora, et al., Nature 322: 32-38 (1986); Parkos, et al., PNAS USA 85: 3319-3323 (1988)). None of these proteins contains the CAAX consensus isoprenylation motif nor have they been reported to be isoprenylated. Expression of cytochrome $b_{558}$ was normal in HL-60 cells treated with 10 $\mu$M compactin, suggesting the treated cell contained adequate levels of dolichol for glycosylation of this membrane protein. Although it is possible that an as-yet unidentified oxidase component unrelated to the LMWG is isoprenylated, our results suggest that it is more probable that it is the regulatory LMWG known to be involved in the oxidase system that is being affected. It has been explicitly demonstrated that various forms of Ras (Hancock, et al., Cell 57: 1167-1177 (1991); Casey, et al., PNAS USA 86: 8323-7 (1989); Schafer, et al., Science 245: 379-384 (1989); Jackson, et al., PNAS USA 87: 3042-6 (1990)), Rap1 (Buss, et al., Mol. Cell. Biol. 11: 1523-1527 (1991); Kawata, et al., PNAS USA 87: 8960-4 (1990)), Rap2 (Winegar, et al., J. Biol. Chem. 266: 4381-6 (1991)), G25 (Yamane, et al., PNAS USA 88: 286-290 (1991)), Rac (Oidsbury, et al., Biochem. Biophys. Res. Commun. 171: 804-812 (1990); Kinsella, J. Biol. Chem. 266: 9786-9794 (1991)), Ral (Kinsella, suora (1991)), and Rab (Kinsella, et al., J. Biol. Chem. 266: 8540-8544 (1991); Khosravi-Far, et al., PNAS USA 88: 6264-6268 (1991)) are isoprenylated posttranslationally.

The present studies made use of the essentially irreversible effect of compactin to inhibit posttranslational isoprenylation to identify the subcellular location of the putative LMWG. Somewhat surprisingly, the compactin-sensitive component was found to reside in the HL-60 cytosol. This was indicated by the ability of the membrane fraction from the compactin-treated cells to fully support a normal respiratory burst, whereas the cytosol from such cells was largely defective in supporting a normal oxidative response. Since analysis of Rap1 indicated that a portion of this GTP-binding protein was still membrane associated after treatment with 10 $\mu$M compactin, it is possible that not all compactin-sensitive membrane components were decreased to rate-limiting levels. These results may be interpreted, however, to indicate that the relevant component (LMWG) required for oxidase activation is resident in the cytosol and that it must be isoprenylated in order to carry out its normal function in supporting a respiratory burst. A preferred hypothesis, as depicted in FIG. 3, is that this protein might have to interface with the membrane at some point during the activation of the oxidase and that the isoprenyl group is necessary for this transient interaction to occur effectively. Alternatively, if this component is a LMWG, it may require this posttranslational modification for efficient interaction with regulatory components, such as guanine nucleotide dissociation stimulators or inhibitors. It is clear from previous work that isoprenylation of a protein is not sufficient in itself for membrane i0 localization. Indeed, many isoprenylated proteins are cytosolic and both Ras and G25K are found in cytosolic and membrane-associated isoprenylated forms. (See, e.g., Winegar, supra (1991). Although the gamma subunits of the heterotrimeric G proteins have been shown to be isoprenylated, the localization of the compactin-sensitive factor to the cytosol would apparently rule out the possibility that the G protein gamma subunit is the necessary factor. G protein B/gamma subunits are membrane localized and B/gamma subunits in human neutrophil cytosol were not detected by Western blotting (Bokoch, et al., J. Cell Biol. 106: 1927-1936 (1988)).

These findings demonstrate the existence of a protein that is required for activity of the NADPH oxidase and whose activity can be inhibited by inhibitors of protein isoprenylation. This protein, which is likely to be a regulatory LMWG, is localized to the HL-60 cytosol. Recent experiments indicate that Rac2 is a likely target sensitive to isoprenylation inhibitors such as compactin and lovastatin. An important area of future investigation will be to further characterize this particular component and to define its role in regulating the NADPH oxidase system. Our results suggest that it may be possible to develop new classes of anti-inflammatory drugs whose targets are the enzymatic machinery that carries out the posttranslational processing of this regulatory component. Similar strategies are currently being pursued in attempts to develop inhibitors of cell transformation caused by the Ras oncogene.

EXAMPLES

The following examples are intended to illustrate, but not limit, the present invention.

EXAMPLE 1

Assay Methods

Culture of HL-60 Cells

HL-60 cells were maintained in stationary culture in RPMI 1640 medium (Gibco, Grand Island, NY) containing 10% fetal bovine serum at 37° C in an atmosphere of 95 air and 5% $CO_2$. The cells (about $8 \times 10^5$/ml) were differentiated into neutrophil-like cells by treatment with 1.3% DMSO for six days (Harris, et al., *J. Leukocyte Biol.* 37: 407–422 (1985)). The cells were treated with the indicated levels of compactin or lovastatin by addition of a 1,000-fold concentrated stock solution to the appropriate concentration on day 4 of differentiation. Similar results were obtained if inhibitors were added at day I of differentiation, but in this case, cell viability was somewhat decreased at higher concentrations of each drug. In studies of the protective effect of mevalonic acid, the compound was added as the mevalonolactone (Sigma Chemical Co., St. Louis, MO) at a concentration of 1 mM to the cell culture on days 4 to 6. Similarly, cholesterol was added in the form of LDL prepared according to the method of Curtiss and Edgington (Curtiss, et al., *J. Biol. Chem.* 257: 15213-15221 (1991)) at a final concentration of 50 μg/ml; ubiquinone (Sigma Chemical Co., St. Louis, MO) was added as Coenzyme Q-10 at a final concentration of 0.5 mM; and dolichol (Sigma Chemical Co., St. Louis, MO) was added as a dispersion in phosphatidylcholine at a final concentration of 0.5 mM (Cutts, et al., *J. Cell Physiol.* 139: 550-555 (1989)).

Preparation of HL-60 Cell Membranes

Cells (about $1-2 \times 10^8$) that had been DMSO-differentiated and treated with ±10 μM compactin were pelleted, washed once with isotonic NaCl, and treated with diisopropyl-fluorophosphate (DFP) for 15 minutes on ice. The cells were then pelleted and resuspended in 10 mM Pipes pH 7.3, 100 mM KCl, 3 mM NaCl, 1 mM ATP, 3.5mM $MgCl_2$ (Relax buffer) plus 100U aprotonin/ml, 1 mM PMSF, and 0.34M sucrose to a final concentration of about $1 \times 10^8$/ml. The cells were then disrupted o ice by $3 \times 10s$ bursts at medium setting with a Heat Systems sonicatorcell disrupter (model W-375; Heat Systems Inc., pellet unbroken cells and nuclei, and the remaining material was centrifuged at 165,000 g for 60 minutes at 2° C. The clear supernatant was collected as HL-60 cytosol. The membrane pellets were resuspended in Relax buffer with aprotonin, PMSF, and sucrose (as above) to a protein concentration of 3-5 mg/ml. Cytosol protein concentrations were typically between 1.5 and 3 mg/ml. Protein values were determined using the BCA assay (Pierce Chemical Co., Rockford, IL) with bovine serum albumin as a standard.

$Q_2$—Assays with Cells or Subcellular Fractions $O_2$—formation by HL-60 cells was assessed by the SOD-sensitive reduction of cytochrome c. Cells were suspended at $1 \times 10^7$/ml in Krebs-Ringer Hepes buffer with 5.5 mM glucose (KRHG) and 50–100μl of cells were added to a cuvette containing 100 μM cytochrome c (type III, Sigma Chemical Co., St. Louis, MO), ±300 μg/ml SOD (Sigma Chemical Co., St. Louis, MO) in 700–750 μl KRHG. Cytochalasin b (Sigma Chemical Co., St. Louis, MO) was added to a final concentration of 5 μg/ml, and the cells were incubated at 37° C. for five minutes while a stable baseline at a wavelength of 550 nm was obtained. $O_2$—formation was initiated by the addition of 1 μM N-formylmethionylleucylphenylalanine (FMLP; Sigma Chemical Co., St. Louis, MO) or 1μg/ml phorbol myristate acetate (PMA; Sigma Chemical Co., St. Louis, MO). Cytochrome c reduction at 550nm was continuously monitored and maximal rate and extent of the reaction calculated.

To assess $O_2$—formation using HL-60 membrane and cytosol, the cell-free system of Curnutte, et al. (Curnutte, et al., *J. Biol. Chem.* 262: 5563-5569 (1987); Curnutte, et al.,m *J. Biol. Chem.* 262: 6450-6452 (1987)) was utilized. Briefly, HL-60 membrane pellet (50–60μg) or human neutrophil membrane ($6.35 \times 10^6$ cell equivalents) was added to a cuvette containing 100 μM cytochrome c (type III, Sigma Chemical Co., St. Louis, MO), 6.25 mM $MgCl_2$, 93 mM KCl, 2.8 mM NaCl, 9.3 mM Pipes pH 7.3, 0.8mM ATP, 0.16 mM NADPH, 10 μM GTPgammaS, 225 μg HL-60 cytosol, or 250 μg ($1 \times 10$; cell equivalents) of human neutrophil cytosol and ±300μg/ml SOD (Sigma Chemical Co., St. Louis, MO). After a three-minute equilibration at 25° C., the formation of $O_2$—was initiated by the addition of 100 μM SDS. $O_2$—generation was monitored continuously as the SOD-sensitive reduction of cytochrome c at 550 nm. Human neutrophil plasma membranes (gamma-GSP) and cytosol (GSS) were prepared as described in (Curnutte, et al., suora (1987)).

Flow Cytometric Analysis of Cell Viability

Cell viability was determined by uptake of propidium iodide (537-059; Calbiochem-Behring Corp., La Jolla, CA), detected from the emission fluorescence at 625/35 nm using a DM560 dichronic mirror (Krishan, *J. Cell. Biol.* 66: 188-192 (1975)). Expression of N-formyl peptide receptor was determined using fluorescein-labeled N-CHONle-Leu-Phe-Nle-Tyr-Lys (Molecular Probes, Inc., Eugene, OR) essentially by the method of Sklar and Finney (Sklar and Finney, *Cytometry* 3: 161-165 (1982)). Specificity of ligand binding was determined in the presence of 4 mM unlabeled T-boc peptide. CD14 expression was determined using monoclonal antibody 3C10 at a dilution of 1:1,000 (see Goyert and Ferrero, in *Leucocyte Typing III: White Cell Differentiation Antigens*, McMichael, ed., Oxford Univ. Press, NY, pp. 613-619 (1988)), with detection using a fluorescein-labeled secondary antibody. Flow cytometric analyses were performed on a FACSIV (registered trademark of Becton-Dickinson, San Jose, CA) equipped with a 2W argon laser (Coherent Inc., Palo Alto, collected in list mode and analyzed using the Consort 30 program (Becton-Dickinson, San Jose, CA) after collecting 10,000 events.

Immunological Procedures

Western blots were performed as described in Bokoch, et al., Cell Biol. 106: 1927-1936 (1988). Anti-Rap1 antibody R61, anti-G protein β subunit antibody R3.4, and anti-cytochrome 22-kD subunit antibody are all specific and are described in Bokoch, et al., Cell Biol. 106: 1927-1936 (1988); Quilliam, et al., J. Immunol. 147: 167 (1991); parkos, et al., J. Clin. Invest. 80: 732-742 (1987), respectively.

Analysis of Rap1 processing in HL-60 cells was performed by labeling cells ($8 \times 10^5$/ml) with 200μCi/ml $^{35}$S-Trans-label (ICN Biomedicals, Inc., Costa Mesa, CA) for 5 days during cell differentiation with 1.3% DMSO in Cys-Met-free medium containing 12% dialyzed fetal bovine serum. Various concentrations of compactin were included as indicated. Metabolically labeled cells were collected, washed once with isotonic NaCl, treated with 2.5 mM Hepes pH 7.5, 100 mM NaCl, 1 mM EDTA, 1 % Triton X-100, 2.5 μM PMSF, and 100U aprotonin. After a 15-minute incubation on ice, the cell lysates were pelleted in a microfuge for 2 minutes and then the supernatant was transferred to clean tubes containing 100 μl 4M NaCl, 5 μl 10% SDS, and 50 μl 10% deoxycholate. The samples were boiled for two minutes, pelleted, and transferred to clean tubes containing 2 μl of the primary antibody, 142-24E05 (Chesa, et al., PNAS USA 84: 3234-3238 (1987); Bokoch, et al., J. Biol. Chem. 263: 16744-16749 (1988)). Immune precipitates were then worked up as previously described (Quilliam, et al., J. Immunol. 147: 167 (1991)), except that the pellets were washed six times with 1 ml 50 mM Hepes pH 7.5, 500mM NaCl, 0.1% Triton X-100, and 0.059% SDS before preparation for SDS-PAGE.

EXAMPLE 2

Inhibition of $O_2$—Generation by Compactin and Lovastatin

The HL-60 cell line is a promyelocytic line that, when induced to differentiate into a neutrophil-like cell by DMSO, develops a fully-activatable NADPH oxidase (Harris, et al., J. Leukocyte Biol. 37: 407-422 (1985); Newburger, et al., J. Biol. Chem. 259: 3771-3776 (1991); Levy, et al., J. Immunol. 145: 2595-2601 (1990); Roberts, et al., J. Cell Biol. 95: 720-726 (1982)).

DMSO-differentiated HL-60 cells were treated with various concentrations of compactin and a dose-dependent inhibition of $O_2$—formation was observed in response to either the receptor stimulus, FMLP, or the protein kinase C activator, PMA (see Table 1 below). Both the rate and the extent of $O_2$-formation were diminished by the drug. Inhibition was half-maximal between 0.4 and 2 μM compactin and reached nearly complete inhibition (>85%) at 10 μM compactin. HL-60 cell viability was not affected by the compactin treatment as assessed by staining with propidium iodide (see Table 1).

TABLE 1

Effects of Compactin on HL-60 Cell Viability, Differentiation, and Respiratory Burst Activity

| Compactin μM | FMLP-stimulated $O_2$— formation | | % viable cells | Percent cell differentiation | |
|---|---|---|---|---|---|
| | Rate % of control | Extent | % | NFPR[c] % | CD14 % |
| 0 | 100 | 100 | 100 | 100 | 100 |
| 0.4 | 77 ± 10 | 71 ± 10 | 100 ± 1.6 | 102[a] | 98[a] |
| 2 | 47 ± 11 | 36 ± 11 | 95 ± 1.2 | 100[a] | 93[a] |
| 4 | 39 ± 4.1 | 22 ± 1.0 | 97 ± 0.9 | 103 ± 2.6 | ND[b] |
| 10 | 15 ± 2.6 | 12 ± 2.1 | 96 ± 1.2 | 97 ± 0.6 | 94[a] |

[a] (n = 2)
[b] ND = not done
[c] NFPR = N-formyl peptide receptor
Values are means ± SEM of three or more experiments, except as indicated.

It has now been noted that compactin inhibits $O_2$—generation in DMSO-differentiated HL-60 cells. The inhibitory effect of compactin on FMLP-stimulated $O_2$—formation could conceivably be due to an effect of the drug to prevent normal HL-60 differentiation into a neutrophil-like cell. It has been previously shown that HL-60 differentiation causes a marked increase in the expression of N-formyl peptide chemoattractant receptor (Niedel, et al., PNAS USA 77: 1000-1004 (1980)). Also, a number of known components of the NADPH oxidase system have been shown to increase upon HL-60 differentiation (Levy, et al., supra (1990); Roberts, et al., suora (1982)). HL-60 differentiation was assessed using two distinct markers: appearance of N-formyl peptide receptors and appearance of the CD14 antigen. Both induction of N-formyl peptide receptor expression and CD14 expression were normal in the compactin-treated cells (see Table 1). The inhibitory effect of compactin on FMLP-stimulated $O_2$—formation was therefore not due to a loss of high affinity cell surface receptors for this chemoattractant. The loss in the ability of PMA to stimulate $O_2$—formation also argued that a process downstream of receptors and their associated heterodimeric G protein was being affected. Since cell differentiation appeared normal, it is also unlikely that other oxidase components were not expressed at normal levels. This was confirmed by analysis of cytochrome $b_{558}$ levels in treated vs. control cells using a specific anti-cytochrome antibody (Parkos, et al., J. Clin. Invest 80: 732-742 (1987)) on Western blots (data not shown).

It was also determined that compactin did not cause inhibition via direct short-term toxic effects upon the NADPH oxidase system. Treatment of peripheral blood neutrophils with 10 μM compactin for up to two hours produced no effect upon the ability of these cells to support a respiratory burst in response to FMLP. Additionally, using a cell-free oxidase system, the inclusion of 10 μM compactin in the assay cuvette did not inhibit $O_2$—formation. Finally, similar inhibition of the NADPH oxidase in HL-60 cells treated with 25 or 50 μM lovastatin, anther inhibitor of HMG-CoA reductase, was observed (data not shown). It seems unlikely that both compounds would randomly produce similar nonspecific toxic effects on the NADPH oxidase.

Our data also indicate that compactin inhibition is specifically reversed by mevalonic acid. Inhibition of protein isoprenylation can interfere with LMWG function without inhibiting overall cellular function (Maltese, supra (1990)). Since compactin inhibits at the enzymatic step preceding mevalonic acid synthesis, one should be able to reverse effects of compactin due specifically to inhibition of this pathway by addition of exogenous mevalonic acid. Addition of 1 mM mevalonic acid (added as the mevalonolactone) to DMSO-differentiated HL-60 cells that had been treated with 4 or 10 μM compactin nearly completely reversed the inhibitory effect of this agent (see Table 2). Mevalonate itself had no consistent effect on control rate or extent of $O_2$—formation, although in several experiments the responses were slightly enhanced. In contrast, the supplementation of the HL-60 cells with 50 μg/ml LDL cholesterol, with ubiquinone 50 (0.5 mM), or with dolichol (0.5 mM) had no effect on compactin blockade of oxidase activity.

TABLE 2

Prevention of Compactin-Inhibition by Mevalonic Acid

| Condition | FMLP-stimulated $O_2$— formation | |
|---|---|---|
| | Rate | Extent |
| | % of control | |
| No addition | 100 | 100 |
| + 1 mM mevalonate | 120 ± 10 | 111 ± 8.0 |
| + 4 μM compactin | 43 ± 5.0 | 28 ± 3.5 |
| 4 μM compactin + 1 mM mevalonate | 97 ± 4.0 | 96 ± 8.0 |
| + 10μM compactin | 19 ± 3.9 | 13 ± 0.4 |
| 10 μM compactin + 1 mM mevalonate | 115 ± 7.6 | 114 ± 1.6 |
| + 50 μg/μl cholesterol | 90[a] | 99[a] |
| 10 μM compactin + 50 μg/ml cholesterol | 28[a] | 22[a] |

[a](n = 2)

Values are means ±SEM of three experiments, except as indicated.

EXAMPLE 3

Compactin Inhibition of LMWG Isoprenylation

Compactin also appears to inhibit LMWG isoprenylation in HL-60 cells. The ability of the concentrations of compactin used to inhibit endogenous HL-60 cell LMWG isoprenylation was assessed. Inhibition of Rap1 isoprenylation was determined in two ways. Western blotting was used to evaluate the presence of Rap1 in cytosol or membrane fractions of compactin-treated vs. untreated cells (see FIG. 1). In FIG. 1, Western blot analysis of Rap1 in HL-60 subcellular fractions is shown. HL-60 cells were treated with ±10 μM compactin, and membrane and cytosol fractions were prepared as described in Example 1. Equal amounts of membrane protein (100 μg) and cytosol protein (70 μg), respectively, were loaded in each lane. Total membrane protein obtained in this experiment from about 3×10[8] cells was about 3 mg and cytosolic protein was about 2 mg. The samples were analyzed on 15% SDS-polyacrylamide gels (SDS-PAGE), transferred to nitrocellulose, and blotted with specific anti-Rap1 antibody, R61, at 1:500 dilution. Detection was with $^{125}$I-goat anti-rabbit IgG and autoradiograms were exposed for 24–36 hours with intensifying screen at −70° C.

In untreated cells, Rap1 was present largely in the membrane fraction, with very little Rap1 in the cytosol. This is consistent with our previous observations on the subcellular distribution of Rap1 in mature human neutrophils (Quilliam, et al., J. Immunol 147: 167 (1991)). In contrast, cells treated with 10 μM compactin showed the appearance of large amounts of Rap1 in the cytosolic fraction It was estimated by densitometric analysis that about 60-70% (n=3) of the total Rap1 previously associated with the membrane pellet was now soluble. This observation is consistent with the ability of isoprenylation to promote membrane association of LMWG. Isoprenylation of Rap1 was also assessed by metabolic labeling of the HL-60 cells with immune precipitation of Rap1, and analysis of the 22kD processed and 23kD unprocessed forms of Rap1 (Buss, et al., Mol. Cell, Biol. 11: 1523-1527 (1991)). These experiments confirmed a dose-dependent decrease in the 22 kD processed form, with a proportional increase in the 23 kD unprocessed (re-isoprenylated) form (data not shown).

EXAMPLE 4

Localization of the Sensitive Factor

Subcellular localization of the compactin-sensitive factor is now feasible. To localize the compactin-sensitive factor required for NADPH oxidase activity to either the cytosol, membrane, or both, subcellular fractions from control or compactin-treated differentiated HL-60 cells were prepared. The membrane fraction and cytosol from the cells were then analyzed using the cell-free NADPH oxidase system. When membrane and cytosol from the untreated HL-60 cells were combined in the cell-free assay, $O_2$—formation in response to 100 μM SDS was rapid and was similar to rates obtained with more purified subcellular fractions obtained from human peripheral blood neutrophils (see Table 3). In contrast, the fractions prepared from the cells pretreated with 10 μM compactin were unable to sustain a normal respiratory burst in vitro, with both the rate and extent of the burst decreased to less than 10% of control values.

TABLE 3

Analysis of $O_2$— Formation by Subcellular Fractions from HL-60 Cells ± Compactin Treatment

| Condition | Rate of $O_2$ formation | | |
|---|---|---|---|
| | Exp. 1 | Exp. 2 | Exp. 3 |
| | (nmol/min) | | |
| Untreated cytosol + untreated membrane | 2.2 | 2.1 | — |
| Compactin cytosol + compactin membrane | 0.1 (1) | 0.4 (5) | — |
| Neutrophil cytosol + neutrophil membrane | 4.5 | 4.7 | 6.8 |
| Neutrophil cytosol + untreated membrane | 2.0 | 2.6 | 4.1 |
| Neutrophil cytosol + compactin membrane | 1.9 (95) | 2.6 (100) | 4.0 (98) |
| Untreated cytosol + neutrophil membrane | 3.3 | 4.0 | 5.1 |
| Compactin cytosol + neutrophil membrane | 1.1 (33) | 1.5 (37) | 2.4 (47) |

HL-60 cells were treated ±10 μM compactin, as described herein. Untreated cytosol/membrane and compactin cytosol/membrane, etc., refer to the fractions obtained from these cells. Values are the result of duplicate determinations within each experiment. Values in parentheses represent the percent of the rate obtained for the respective untreated HL-60 sample.

Figure 2:
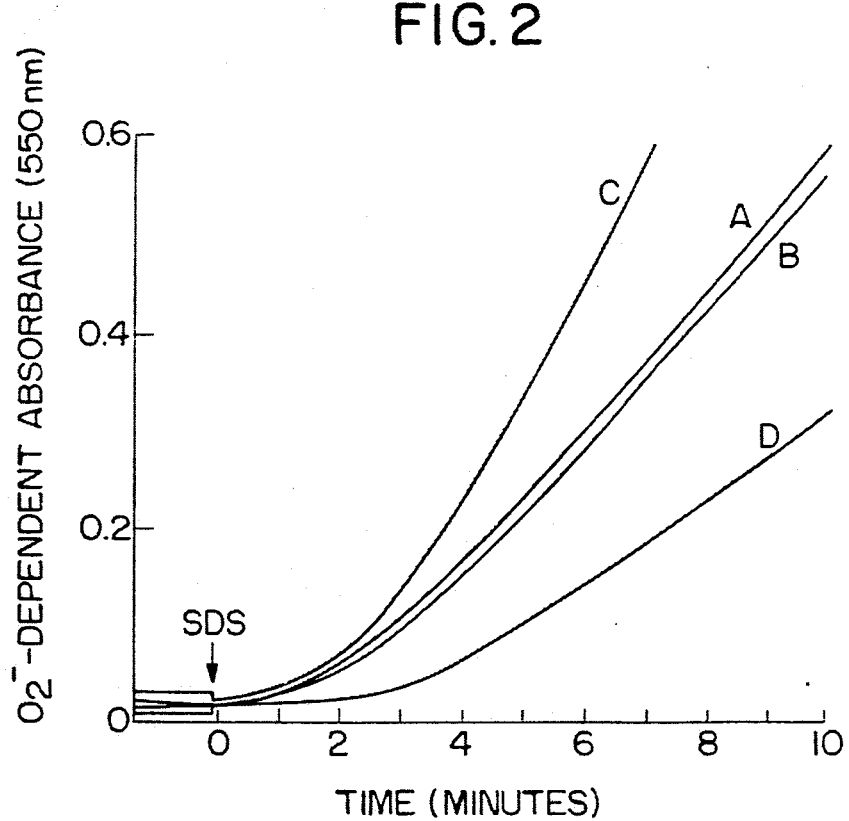
FIG. 2 illustrates a complementation analysis of $O_2-$ formation by control vs. compactin-treated HL-60 cells (with $O_2-$ formation analyzed as described below). Line A represents untreated HL-60 membrane +neutrophil GSS; line B represents compactin-treated HL-60 membrane neutrophil GSS; line C represents untreated HL-60 cytosol +neutrophil gamma GSP; line D represents compactin-treated HL-60 cytosol +neutrophil gamma GSP. $O_2-$-dependent absorbance (550nm) is plotted against time in minutes.

Whether the inhibited factor(s) was present in the membrane fraction or cytosol was determined via performing complementation experiments using cytosol or membranes from normal human neutrophils. Data from these experiments is illustrated above in Table 3 and in FIG. 2. FIG. 2 illustrates complementation analysis of $O_2$-formation by control versus compactin-treated HL-60 cells. $O_2$—formation was analyzed in a cell-free assay as described in the Examples. Line A represents untreated HL-60 membrane +neutrophil GSS; line B represents compactin-treated HL-60 membrane+neutrophil GSS; line C represents untreated HL-60 cytosol+neutrophil gamma GSP; line D represents compactin-treated HL-60 cytosol+neutrophil gamma GSP.

The combination of membrane from the compactin-treated HL-60 cells with cytosol from normal neutrophils gave a rate of $O_2$-formation that was essentially identical to that obtained with an equal amount of cytosol (protein/protein) from untreated HL-60 cells. This rate was slightly less than the rate obtained with both membrane and cytosol from control neutrophils, but the data have not been adjusted for the difference in purity and protein value between the highly purified neutrophil membranes and the relatively crude HL-60 membranes. It was apparent that the compactin treatment of the HL-60 cells, somewhat surprisingly, had not affected a membrane-associated oxidase component. When cytosol from the compactin-treated HL-60 cells was used with membranes from normal neutrophils, however, the ability to form $O_2$—was markedly reduced over that obtained with an equivalent amount of cytosol from untreated HL-60 cells. The rate of $O_2$— formation was decreased to about one-third of that seen with the untreated HL-60 cytosol. Additionally, as can be seen in FIG. 2, not only was the rate of $O_2$—formation decreased, but there was also a marked increase in the lag period that occurs after the addition of the SDS and until the rate of $O_2$—formation becomes maximum. It was apparent that the compactin-sensitive point in $O_2$—formation was localized to a factor present in the HL-60 cell cytosol.

The foregoing is intended to be illustrative of the present invention, but not limiting. Numerous variations and modifications may be effected without departing from the true spirit and scope of the invention.

We claim:

1. A method of inhibiting respiratory burst in a patient in need of such treatment, comprising administering a composition comprising an effective amount of an isoprenylation inhibitor and a pharmaceutically acceptable carrier or excipient to said patient.

2. The method of claim 1, wherein said inhibitor is selected from the group consisting of lovastatin, compactin, and fluoromevalonate.

3. The method of claim 2, wherein said effective amount is in the range of up to 200 mg per day.

4. The method of claim 3, wherein said effective amount is in the range of 10 mg to 40 mg per day.

5. The method of claim 3, wherein said effective amount is in the range of 20 mg to 80 mg per day.

6. The method of claim 1, wherein said composition is administered orally.

7. The method of claim 1, wherein said inhibitor specifically targets a GTP-binding protein.

8. The method of claim 7, wherein said protein is a low molecular weight GTP-binding protein (LMWG).

9. The method of claim 1, wherein said inhibitor comprises a terpene.

10. The method of claim 9, wherein said terpene is selected from the group consisting of limonene, perillic acid, and dihydroperilllic acid.

11. The method of claim 9, wherein said effective amount is an amount sufficient to raise the terpene concentration in the blood of said patient to at least 0.05 mM.

12. The method of claim 9, wherein said effective amount is an amount sufficient to raise the terpene concentration in the blood of said patient to at least 0.1 mM.

13. The method of claim 9, wherein said effective amount is an amount sufficient to raise the terpene concentration in the blood of said patient to at least 5 mM.

14. The method of claim 9, wherein said terpene concentration in the blood of said patient does not exceed 50 mM.

* * * * *